United States Patent [19]

Gunderson

[11] Patent Number: 5,776,142
[45] Date of Patent: Jul. 7, 1998

[54] CONTROLLABLE STENT DELIVERY SYSTEM AND METHOD

[75] Inventor: Richard C. Gunderson, Maple Grove, Minn.

[73] Assignee: Medtronic, Inc., Minneapolis, Minn.

[21] Appl. No.: 845,780

[22] Filed: Apr. 25, 1997

Related U.S. Application Data

[60] Provisional application No. 60/033,511, Dec. 19, 1996.

[51] Int. Cl.⁶ ............................ A61F 11/00; A61M 29/00
[52] U.S. Cl. ............................ 606/108; 606/198; 623/1
[58] Field of Search ................... 606/1, 108, 191–200; 623/1, 11, 12

[56] References Cited

U.S. PATENT DOCUMENTS

| | | |
|---|---|---|
| 4,553,545 | 11/1985 | Maass et al. . |
| 4,665,918 | 5/1987 | Garza et al. . |
| 4,771,773 | 9/1988 | Kropf . |
| 5,160,341 | 11/1992 | Brenneman et al. . |
| 5,246,445 | 9/1993 | Yachia et al. . |
| 5,372,600 | 12/1994 | Beyar et al. . |
| 5,433,723 | 7/1995 | Lindenberg et al. . |
| 5,456,667 | 10/1995 | Ham et al. .................. 606/198 |
| 5,458,615 | 10/1995 | Klemm et al. . |
| 5,476,505 | 12/1995 | Limon . |
| 5,669,932 | 9/1997 | Fischell et al. .............. 606/198 |
| 5,700,269 | 12/1997 | Pinchuk et al. .............. 606/198 |

*Primary Examiner*—Glenn K. Dawson
*Attorney, Agent, or Firm*—Daniel W. Latham; Harold R. Patton

[57] ABSTRACT

Systems and methods for delivering a radially expandable stent for implantation within a body vessel that provide for the controlled radial expansion of the stent simultaneous with controlled axial movement of the ends of the stent, whereby controlled delivery of the stent can be accomplished. The device may include a screw rotated to simultaneously radially expand and axially compress a stent that has been previously wound onto a delivery device.

22 Claims, 5 Drawing Sheets

CONTROLLABLE STENT DELIVERY SYSTEM AND METHOD

FIELD OF THE INVENTION

The present invention relates to intraluminal stent implants for maintaining a passageway through body vessels in humans and animals. More particularly, the present invention provides a system and method for the controlled release of a self-expanding intraluminal stent within a body vessel.

BACKGROUND OF THE INVENTION

Intraluminal stents can be used to maintain passageways through body vessels in both animal and humans. To do so, the stents typically provide support about a central axial opening to allow the passage of fluids and other substances through the stent. Although stents can be used in many different body vessels, one common application is in blood vessels.

Percutaneous transluminal coronary angioplasty (PTCA) is used to reduce arterial build-up of cholesterol fats or atherosclerotic plaque in blood vessels. Typically a first guidewire is steered through the vascular system to the site of therapy. A guiding catheter, for example, can then be advanced over the first guidewire to the stenosis and the first guidewire is then removed. A balloon catheter on a smaller 0.014 inch diameter second guidewire is advanced within the guiding catheter. When the balloon is in the desired location, it is inflated causing the site of the stenosis to widen. The dilatation of the occlusion, however, can form flaps, fissures and dissections which threaten reclosure of the dilated vessel or even perforations in the vessel wall. Implantation of a stent after dilatation can provide support for such flaps and dissections and thereby prevent reclosure of the vessel or provide a patch repair for a perforated vessel wall until corrective surgery can be performed. Reducing the possibility of restenosis after angioplasty reduces the likelihood that a secondary angioplasty procedure or a surgical bypass operation will be necessary.

An implanted prosthesis, such as an intraluminal stent, can preclude additional procedures and maintain vascular patency by mechanically supporting dilated vessels to prevent vessel collapse. Stents can also be used to repair aneurysms, to support artificial vessels as liners of vessels or to repair dissections. Stents are suited to the treatment of any body lumen, including the vas deferens, ducts of the gallbladder, prostate gland, esophagus, urethra, trachea, bronchus and liver. The body lumens range in size from small coronary vessels to large vessels such as the aortic vessel. The invention applies to acute and chronic closure or reclosure of body lumens.

A typical stent is a cylindrically shaped wire formed device intended to act as a permanent or temporary prosthesis. A typical stent ranges from 5 millimeters to 150 millimeters in length. A stent is deployed in a body lumen from a radially compressed configuration into a radially expanded configuration which allows it to contact and support a body lumen. The stent can be made to be radially self-expanding or expandable by the use of an expansion device. A self expanding stent is typically made from a resilient springy material which, when released, expands radially outward into contact with the body lumen thereby forming a supporting relationship with the vessel walls. Examples of such stents are described in, e.g., U.S. Pat. Nos. 5,246,445 to Yachia et al. and 5,372,600 to Beyar et al.

Typical delivery devices used in connection with self-expanding stents do not allow for the controlled release of the stent at the delivery site within a body vessel. Rather, the stent is typically released in an abrupt fashion and quickly expands to its maximum radial dimensions within the body vessel. U.S. Pat. No. 4,553,545 to Maass et al. discloses a delivery system in which the axial movement of the stent during delivery is not controlled simultaneously with the rotation of the ends of the stent about the longitudinal axis. As a result, the system cannot provide for controlled delivery of the stent.

SUMMARY OF THE INVENTION

It is an object of the invention to provide a system for delivering a radially expandable stent for implantation within a body vessel that provides for the controlled radial expansion of the stent simultaneous with controlled axial movement of the ends of the stent, whereby controlled delivery of the stent can be accomplished.

It is a further object of the invention to provide for the controlled release of the ends of the stent in combination with the controlled rotational and axial movement of the stent.

In one aspect the present invention provides a system for delivering a radially expandable stent for implantation within a body vessel, the system including an elongated tubular member comprising an inner sheath having a proximal end and a distal end and an outer sheath having a proximal end and a distal end, the outer sheath having a lumen for at least partially receiving the inner sheath, the distal end of the inner sheath extending past the distal end of the outer sheath; a self-expanding intraluminal stent located over the distal end of the inner sheath, the stent having a proximal end attached to the distal end of the outer sheath and a distal end attached to the distal end of the inner sheath; and means for controllably rotating the inner sheath relative to the outer sheath and simultaneously controllably moving the inner sheath axially relative to the outer sheath.

In another aspect the present invention provides a system for delivering a radially expandable stent for implantation within a body vessel, the system including an elongated tubular member comprising an inner sheath having a proximal end and a distal end and an outer sheath having a proximal end and a distal end, the outer sheath having a lumen for at least partially receiving the inner sheath, the distal end of the inner sheath extending past the distal end of the outer sheath; a self-expanding intraluminal stent located over the distal end of the inner sheath, the stent having a proximal end attached to the distal end of the outer sheath and a distal end attached to the distal end of the inner sheath; a first handle operatively attached to the inner sheath, the first handle located at the proximal end of the inner sheath; a second handle operatively attached to the outer sheath, the second handle located at the proximal end of the outer sheath; and the first and second handles being operatively mounted on a screw such that rotation of one handle relative to the other handle results in controlled axial movement of the inner and outer sheaths relative to each other.

The present invention provides methods for delivering a radially expandable stent for implantation within a body vessel including steps of providing a stent delivery device including an elongated tubular member comprising an inner sheath having a proximal end and a distal end and an outer sheath having a proximal end and a distal end, the outer sheath having a lumen for at least partially receiving the inner sheath, the distal end of the inner sheath extending past the distal end of the outer sheath; a self-expanding intraluminal stent located over the distal end of the inner sheath, the stent having a proximal end retained against the distal end of the outer sheath and a distal end retained against the distal end of the inner sheath; and means for controllably rotating the inner sheath relative to the outer sheath and simultaneously controllably moving the inner sheath axially relative to the outer sheath. The next step is inserting the stent delivery device to locate the stent in a desired position within a body lumen, followed by rotating the inner sheath and outer sheath relative to each other, whereby the stent is expanded radially. After the stent has been expanded, the proximal and distal ends of the stent are released.

In another method, the present invention also provides for delivering a radially expandable stent for implantation within a body vessel including the steps of providing a stent delivery device having an elongated tubular member comprising an inner sheath having a proximal end and a distal end and an outer sheath having a proximal end and a distal end, the outer sheath having a lumen for at least partially receiving the inner sheath, the distal end of the inner sheath extending past the distal end of the outer sheath; a self-expanding intraluminal stent located over the distal end of the inner sheath, the stent having a proximal end retained against the distal end of the outer sheath and a distal end retained against the distal end of the inner sheath; a first handle operatively attached to the inner sheath, the first handle located at the proximal end of the inner sheath; a second handle operatively attached to the outer sheath, the second handle located at the proximal end of the outer sheath; and the first and second handles being operatively mounted on a screw such that rotation of one handle relative to the other handle results in controlled axial movement of the inner and outer sheaths relative to each other. The stent delivery device is then inserted to locate the stent in a desired position within a body lumen; and the first and second handles are rotated relative to each other using the screw, whereby the stent is expanded radially. After the stent has been expanded, the proximal and distal ends of the stent are released.

These and other features and advantages of the present invention are described below in connection the description of the preferred embodiments.

DETAILED DESCRIPTION OF THE PREFERRED EMBODIMENTS

The stent delivery device according to the present invention can be used to deliver and controllably expand a self-expanding intraluminal stent within a body vessel. Although the following discussion, along with the figures, describe one embodiment of a stent delivery device manufactured according to the present invention, those skilled in the art will understand that other structures could also be used to accomplish the desired functions of controlled axial movement of the ends of the stent towards each other while simultaneously controllably rotating the ends of the stent about the longitudinal axis to provide for its controlled radial expansion.

Regardless of the actual structure employed, the present invention provides a device for delivering a self-expanding stent that includes means for controllably rotating an inner sheath relative to the outer sheath and simultaneously controllably moving the inner sheath axially relative to the outer sheath. By so doing, the present invention provides the ability to actively control the deployment of a self-expanding stent to prevent its abrupt release within a body vessel. Furthermore, by providing for the combination of controlled simultaneous rotation and axial movement of the stent during implantation, the surgeon may be better able to focus on proper placement of the stent rather than also trying to control its rate of radial expansion and/or axial contraction.

FIGS. 1–6 depict various portions and views of the proximal and distal ends and connecting elongated tubular member of one stent delivery device according to the present invention.

Figure 1:
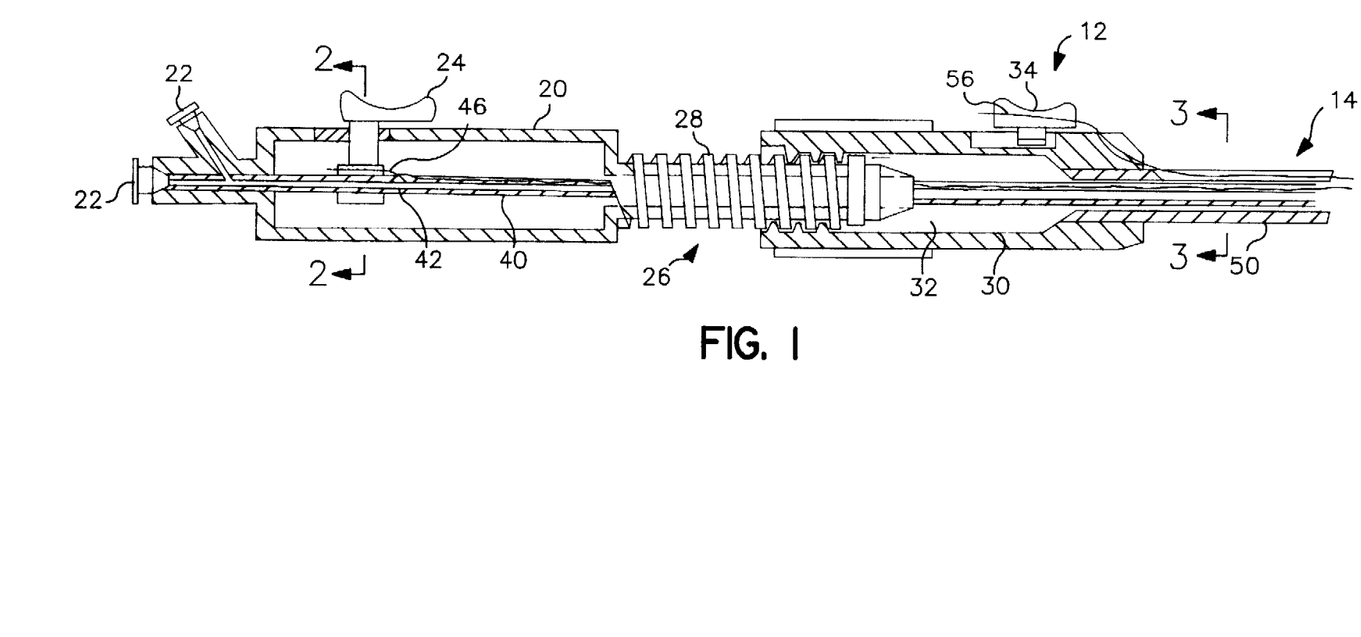
FIG. 1 is a cross-sectional view of the proximal end of one stent delivery device according to the present invention.

Turning to FIG. 1, the proximal end 12 of the stent delivery device includes a first handle 20 attached to an inner sheath 40 and a second handle 30 attached to an outer sheath 50. Inner and outer sheaths 40 and 50 collectively provide an elongated tubular member 14 that extends between the proximal and distal ends of the device.

The diameter of the elongated tubular member 14 can vary according to the intended use of the stent delivery device, i.e., they can be smaller where the intended use is to deliver a relatively small stent and larger for delivering a larger stent. It will also be understood that the diameter of the tubular member 14 can be fixed over its length or, alternatively, the diameter of the tubular member 14 (and the corresponding diameters of inner and outer sheaths 40 and 50) may vary along the length of the elongated tubular member 14.

The first handle 20 includes preferably includes one or more ports 22 for receiving, e.g., guidewires or other devices to assist in guiding a stent to a desired location within a body lumen. Inner sheath 40 preferably extends through handle 20 to the ports 22 as shown and also preferably includes a primary lumen 42 in communication with the openings in the ports 22. Handle 20 also preferably includes a release wire actuator 24 attached to the proximal end of a release wire 46 described more completely below. The actuator 24 is preferably mounted for movement along the longitudinal axis of the stent delivery device.

The handle 20 is preferably fixedly attached to the inner sheath 40 such that rotation of the handle 20 about the longitudinal axis of the device results in corresponding rotation of the inner sheath 40. The handle 20 also preferably includes a screw portion 26 including threads 28 as shown in FIG. 1.

The second handle 30 preferably includes a threaded opening 32 designed to receive the threads 28 of the screw portion 26 of the first handle 20. Handle 30 is fixedly attached to the outer sheath 50 such that rotation of the handle 30 about the longitudinal axis of the device results in corresponding rotation of the outer sheath 50. Handle 30 also preferably includes a release wire actuator 34 attached to the proximal end of a release wire 56 described more completely below. The actuator 34 is preferably mounted for movement along the longitudinal axis of the stent delivery device.

With the two handles 20 and 30 fixedly attached to the inner and outer sheaths 40 and 50, it will be understood that rotation of the handles 20 and 30 relative to each other will cause corresponding relative rotation between the inner and outer sheaths 40 and 50. The screw portion 26 of handle 20 and corresponding screw receiving portion 32 of handle 30, it will also be understood that relative rotation of the handles 20 and 30 will also cause relative movement along the longitudinal axis of the device between the inner and outer sheaths 40 and 50 as will be discussed in more detail below.

Figure 2:
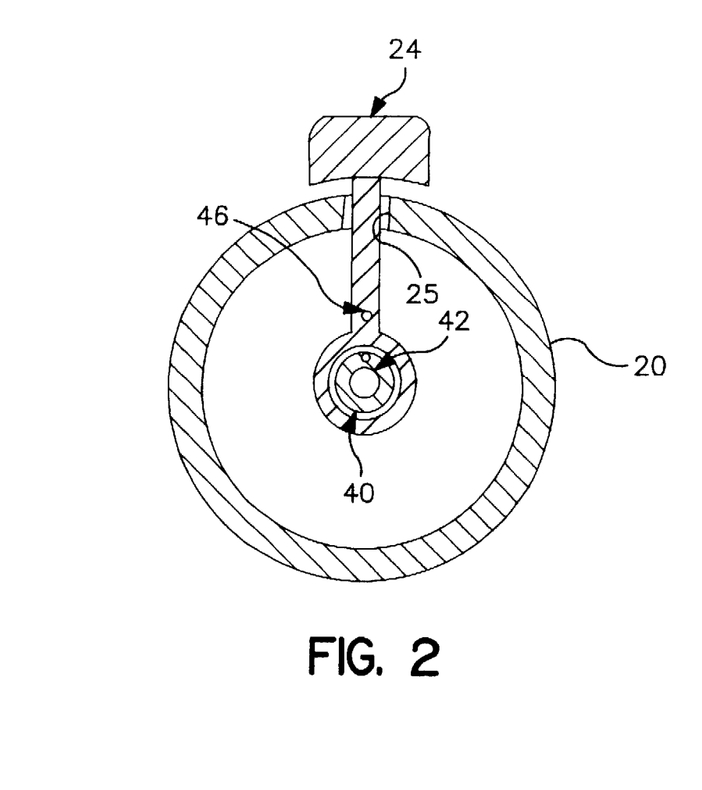
FIG. 2 is a cross-sectional view of the device of FIG. 1, taken along line 2—2.

FIG. 2 is a enlarged cross-sectional view along line 2—2 in FIG. 1 and depicts the first handle 20, inner sheath 40 with primary lumen 42, release wire actuator 24, and release wire 46. As shown in this embodiment, the release wire actuator 24 fits over the inner sheath 40 and within a slot 25 within handle 20.

Figure 3:
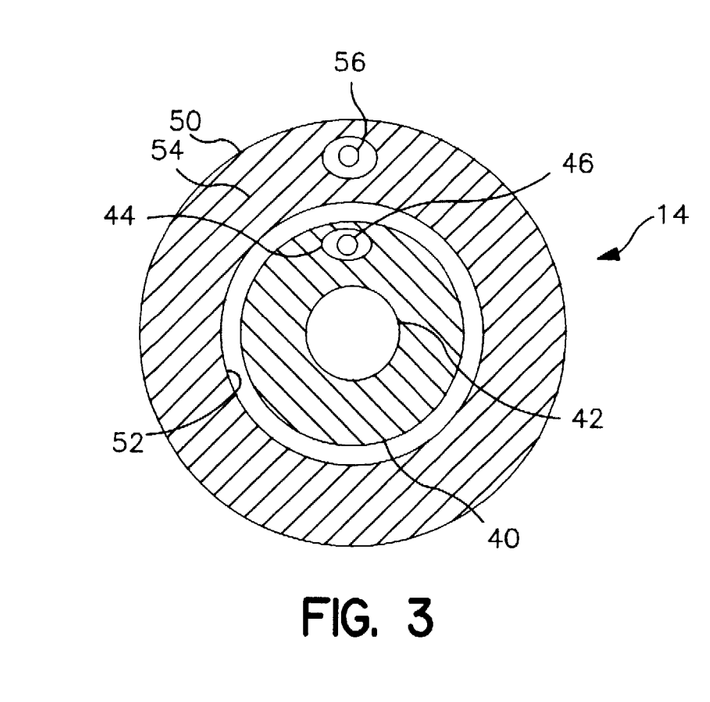
FIG. 3 is a cross-sectional view of the device of FIG. 1, taken along line 3—3.

FIG. 3 is an enlarged cross-sectional view of the elongated tubular member 14 that extends between the proximal end 12 and distal end 16 of the depicted stent delivery device. The member 14 preferably includes an inner sheath 40 having a primary lumen 42 for receiving a guidewire, other device, and/or for delivering a fluid. Inner sheath 40 also preferably includes a release wire lumen 44 for receiving a release wire 46.

Although not shown, it will be understood that the stent delivery device may include one or more seals, valves, etc. to prevent leakage of fluids from the distal end 16 towards the proximal end 12 of the device.

The elongated tubular member 14 also includes an outer sheath 50 having a lumen 52 sized to receive the inner sheath 40 therein. The relative sizes of the inner diameter of lumen 52 and outside diameter of the inner sheath 40 should be such that relative rotation of the inner sheath 40 and outer sheath 50 is allowed. Outer sheath 50 also preferably includes a release wire lumen 54 for receiving a release wire 56 therein.

The inner and outer sheaths 40 and 50 making up tubular member 14 can be made of any suitable material possessing the desired strength, flexibility, rigidity (both longitudinally and torsionally), etc. Examples of suitable materials include, but are not limited to: polymers, braided polymers, co-extruded polymers, metals (e.g., hypo-tubing), etc.

Figure 4:
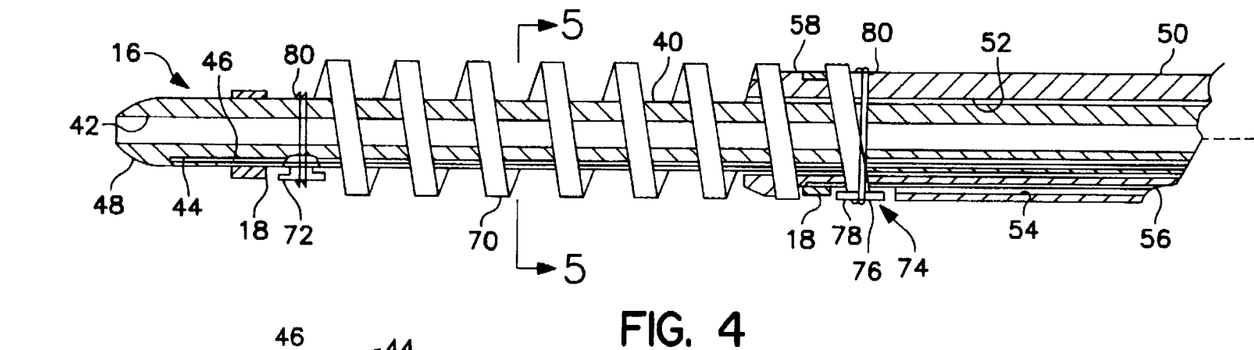
FIG. 4 is a cross-sectional view of the distal end of one stent delivery device according to the present invention, with a self-expanding stent mounted thereon.

Turning now to FIG. 4, the distal end 16 of one stent delivery device according to the present invention will be described. The distal end 16 of the device includes the distal end 48 of the inner sheath 40 (see FIG. 1) as well as the distal end 58 of the outer sheath 50. Also mounted on the distal end 16 of the device is a self-expanding intraluminal stent 70 having a distal end 72 attached to the distal end 48 of the inner sheath 40 and a proximal end 74 attached to the distal end 58 of the outer sheath 50.

Also shown in FIG. 4 is the primary lumen 42 in the inner sheath 40 that allows for the introduction of the device over a guidewire or the simultaneous introduction of other devices through the lumen 42. FIG. 4 also depicts the release wire lumen 44 within which release wire 46 is located. The release wire 46 extends from the proximal end of the device (seen in FIG. 1) to the distal end 16 of the device and terminates near the distal end 72 of the stent 70 where it is used to retain the distal end 72 until release is desired (as will be discussed more completely below).

FIG. 4 also depicts the lumen 52 in outer sheath 50 within which inner sheath 40 is located. Outer sheath 50 also includes a release wire lumen 54 within which release wire 56 is located. The release wire 56 extends from the proximal end of the device (seen in FIG. 1) to the distal end 16 of the device and terminates near the proximal end 74 of the stent 70 where it is used to retain the proximal end 74 until release is desired (as will be discussed more completely below).

Also depicted in FIG. 4 are markers 18 used to locate the position of the stent 70 within a body lumen during insertion and delivery. The markers are preferably radio-opaque or capable of indicating position by some other method. Although two markers 18 are shown, it will be understood that only one marker could be provided or that the device not include any markers 18.

Figure 5:
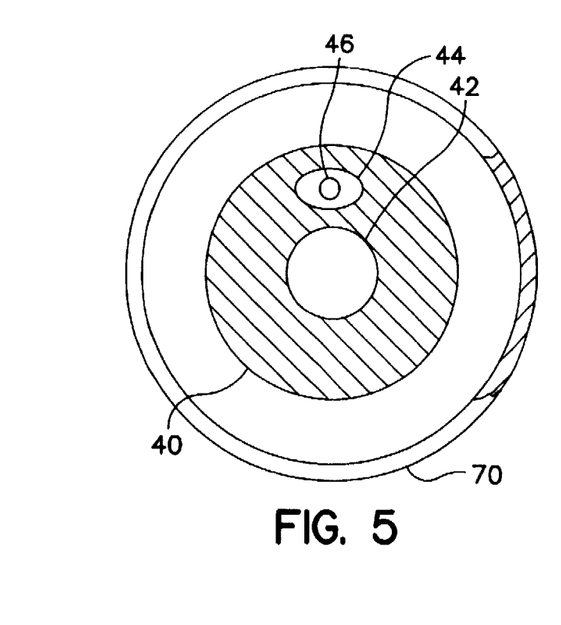
FIG. 5 is a cross-sectional view of the device of FIG. 4, taken along line 5—5.

FIG. 5 is an enlarged cross-sectional view of the distal end of the device of FIG. 4 taken along line 5—5. Included in that view is the inner sheath 40 with its primary lumen 42, release wire lumen 44 and release wire 46. Also depicted is the stent 70 shown slightly expanded, i.e., raised from the surface of the inner sheath 40.

Figure 6:
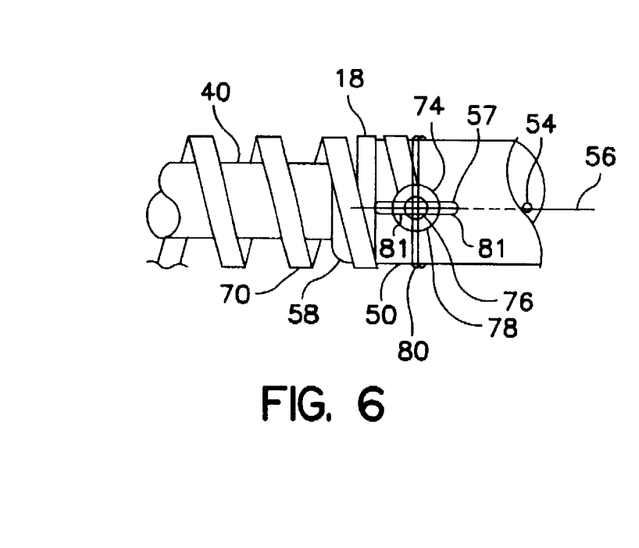
FIG. 6 is an enlarged view of one method of attaching an end of a stent to the stent delivery device according to the present invention.

Turning now to FIG. 6, one mechanism for attaching the ends of the stent 70 to the distal end 16 of the depicted embodiment of a stent delivery device according to the present invention will be described in more detail. The proximal end 74 of the stent 70 is shown in FIG. 6 as attached to the distal end 58 of the outer sheath 50. The distal end 72 of the stent 70 is preferably attached to the distal end 48 of the inner sheath in a similar manner that will not be described herein.

The proximal end 74 of the stent is positioned over an opening 57 formed through the wall of the outer sheath 50. The opening 57 exposes the release wire lumen 54. The end 74 of the stent includes an opening 76 formed therein. A length of suture 80 is looped over two sides of the end 74 of the stent 70 and around the release wire 56 through the opening 57 with two loops 81. As a result, the end 74 of the stent 70 can be retained in the desired position on the distal end 58 of the outer sheath 50. It may also be preferable that the suture 80 extend about the outer diameter of the outer sheath 50 as shown to assist in retaining the end 74 of the stent 70 in the desired location.

To release the end 74 of the stent 70, the release wire 56 is moved proximally to release the loops 81 of the suture 80, thereby releasing the end 74 of the stent 70.

It is preferred that the stent 70 include openings formed at its ends to facilitate secure attachment of the stent 70 to the distal end 16 of the device during delivery of the stent 70. The depicted opening 76 in the end 74 of the stent 70 is formed in a disk-shaped portion 78 of the stent 70 that can also be seen in FIG. 4. The disk-shaped portion 78 can be formed by any suitable method. One method used in connection with the present invention involves welding or soldering a ball of material on the end 74 of the stent 70, machining the ball to form the disk 78 and forming the opening 76 by drilling or any other suitable method.

It will be understood that the depicted method of attaching the ends of the stent 70 to the distal end 16 of the device is illustrative only, and that many other methods of attaching stents to the stent delivery device could be substituted. Examples of other potentially suitable methods for attaching a stent to the stent delivery device of the present invention include those described in U.S. Pat. Nos. 5,246,445 to Yachia et al. and 5,372,600 to Beyar et al.

It is preferred, but not required, that the ends of the stent be attached in a manner that allows for their selective release, although it will be understood that the ends could be retained by hooks or other devices that automatically release the ends of the stent when the tension in the stent is removed by expansion of the stent as described more fully below. If selective release of the ends of the stent is provided for, the user has the opportunity to determine, before release, whether the stent is properly positioned and, if not, reverse the rotation of the inner and outer sheaths to reduce the diameter of the stent and reposition it.

Figure 7:
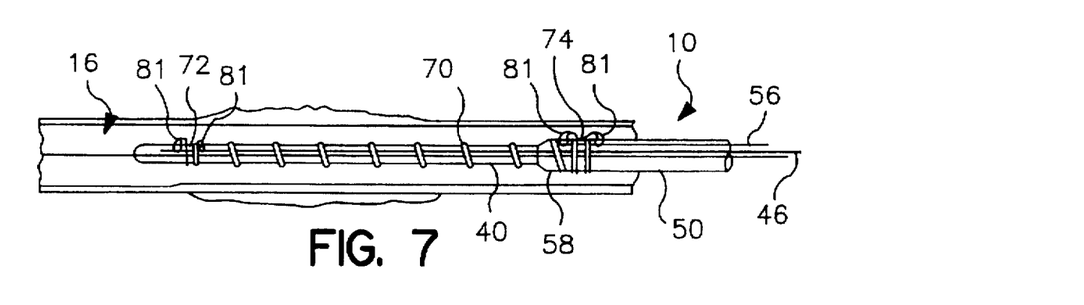
FIGS. 7–10 depict one method of delivering a self-expanding stent using one stent delivery device according to the present invention.

FIGS. 7–10 depict one method of using one stent delivery device 10 according to the present invention. As shown in FIG. 7, the distal end 16 of the device 10 is advanced through a body lumen until the stent 70 is in a desired position. As discussed above, markers (see 18 in FIG. 4) can be provided to assist in accurate placement of the stent 70 within the body lumen. Although the depicted location is a constricted portion of a blood vessel, it will be understood that the device 10 could be used to deliver a stent 70 to any desired location.

As shown in FIG. 7, before delivery of the stent 70, it is preferred that the stent 70 be wound around the portion of the inner sheath 40 extending from the distal end 58 of the outer sheath 50. That configuration is preferred because it provides the smallest profile for the device 10 as its distal end 16 is advanced to the delivery site. In some instances, however, the stent 70 need not be tightly wrapped about the inner sheath 40 as shown in FIG. 7.

The stent 70 is tightly wrapped about the inner sheath 40 by securing its proximal end 74 to the distal end 58 of the outer sheath 50 and securing its distal end 72 to the inner sheath 40. This is preferably performed with the stent 70 in a relaxed or expanded configuration. Once the ends 72 and 74 of the relaxed or expanded stent 70 are firmly attached, the inner sheath 40 and attached distal end 72 of the stent 70 are rotated and simultaneously moved way from the distal end 58 of the outer sheath 50. As a result, the longitudinal length of the stent 70 increases while its outside diameter decreases.

Figure 8:
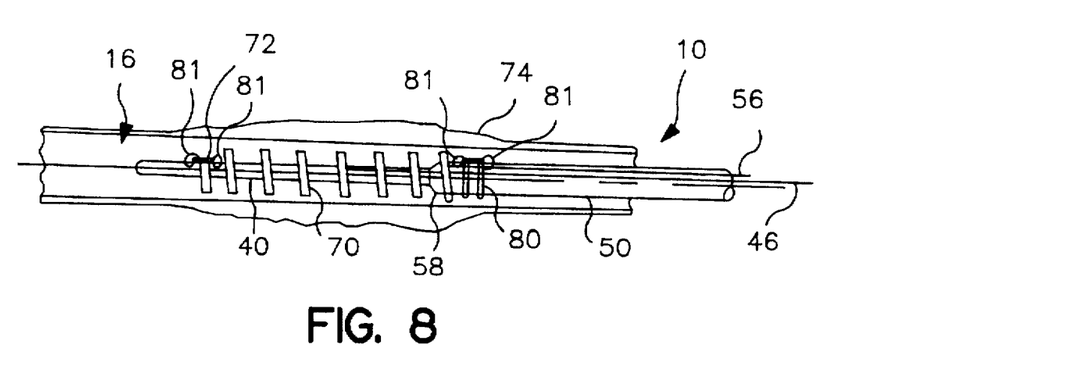

It should be understood that the stent delivery device depicted in FIGS. 1 and 4 illustrates the stent 70 in an at least partially expanded configuration as seen in, e.g., FIG. 8. If the stent 70 were in the tightly wound state as depicted in FIG. 7, the screw portion 26 of the handle 20 would be located further into the threaded opening 32 in second handle 30. Thus, the handle positions shown in FIG. 1 would approximate the handle position during the portion of delivery sequence depicted in FIG. 8.

Once in position, the first handle 20 (see FIG. 1) is rotated about the longitudinal axis such that the handle 20 and attached inner sheath 40 are moved proximally along the longitudinal axis of the tubular member 14, i.e., they are moved away from the distal end 16 of the device 10. In the depicted embodiment, that rotation of the handle 20 and inner sheath 40 would be counter-clockwise when viewed from the proximal end 12 of the device 10. Alternatively, the second handle 30 could be rotated relative to the first handle 20 which would cause the distal end 58 of the outer tube 50 to move towards the distal end 16 of the device 10, i.e., the handle 30 and outer sheath 50 are moved away from the proximal end 12 of the device 10. In the depicted embodiment, that rotation of the handle 30 and outer sheath 50 would be clockwise when viewed from the proximal end 12 of the device 10. In a further alternative, both handles 20 and 30 could be rotated simultaneously. Movement of one handle relative to the other may, however, be preferred because the location of one end of the stent 70 would then presumably remain constant relative to the delivery site.

Referring now to FIG. 8, the stent 70 is shown expanded, i.e., after some relative rotation of the handles 20 and 30 and inner and outer sheaths 40 and 50. The stent 70 is preferably expanded until the outer diameter of the stent 70 is in contact with surrounding tissue.

Figure 9:
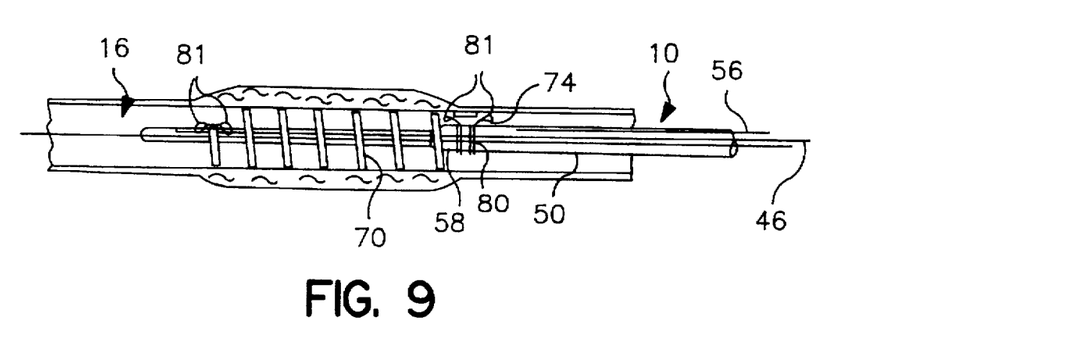

FIG. 9 depicts the stent 70 after the proximal end 74 has been released from the distal end 58 of the outer sheath 50. As seen in FIG. 9, the proximal end 74 is then moved outward, away from the surface of the outer sheath 50 upon release. The release is accomplished by withdrawing the release wire 56 within release wire lumen 54 (see FIGS. 1 and 6) such that the loops 81 of the sutures 80 no longer retain the proximal end 74 of the stent 70.

Figure 10:
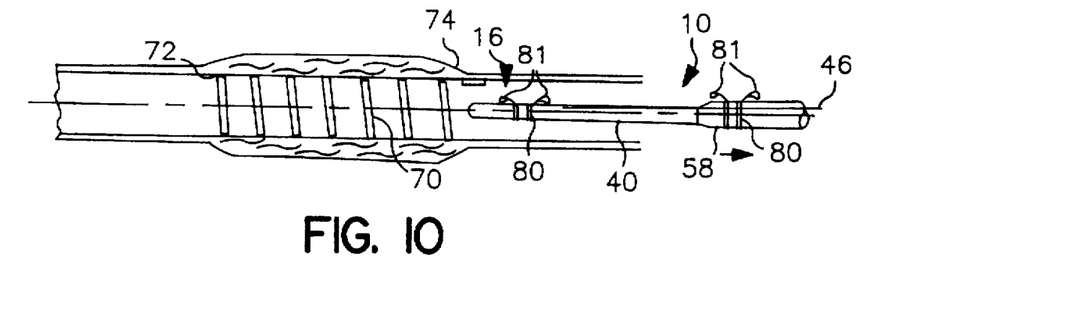

FIG. 10 depicts the stent 70 after the distal end 72 has been released from the inner sheath 40 with the distal end 72 moved outward. The end 72 is also released by movement of a release wire 46 (see FIG. 1) proximally to release the sutures holding the end 72 in place on the inner sheath 40. The inner sheath 40 and outer sheath 50 are also shown as being partially withdrawn from the stent 70 in FIG. 10. Although FIGS. 9 and 10 depict sequential release of the ends 72 and 74 of the stent 70, with the proximal end 74 being released first, it will be understood that the distal end 72 could be released first or that both ends 72 and 74 could be released simultaneously.

The various portions of the stent delivery device 10 and stent 70 delivered using the device described above are all preferably manufactured of any suitable materials. The stents 70 could be manufactured of a variety of materials providing the desired resiliency such that they are self-expanding when released from the device. Examples of such materials including, but not limited to: stainless steel, tantalum, titanium, nickel-titanium alloy, plastics, etc.

The geometry of the stent 70 can also vary depending on the desired application, provided the stent 70 is in the form of a helical coil spring that can be wound and unwound about a longitudinal axis. The pitch or spacing of the coils can vary between stents 70 or within a single stent (see, e.g., U.S. Pat. Nos. 5,246,445 to Yachia et al. And 5,372,600 to Beyar et al.), although it should be noted that the pitch of the threads 28 used to operatively connect the inner and outer sheaths 40 and 50 may need to be varied based on the design of the stent 70. In one example, the pitch of the threads 28 may match the pitch of the coils in the stent 70.

Figure 11:
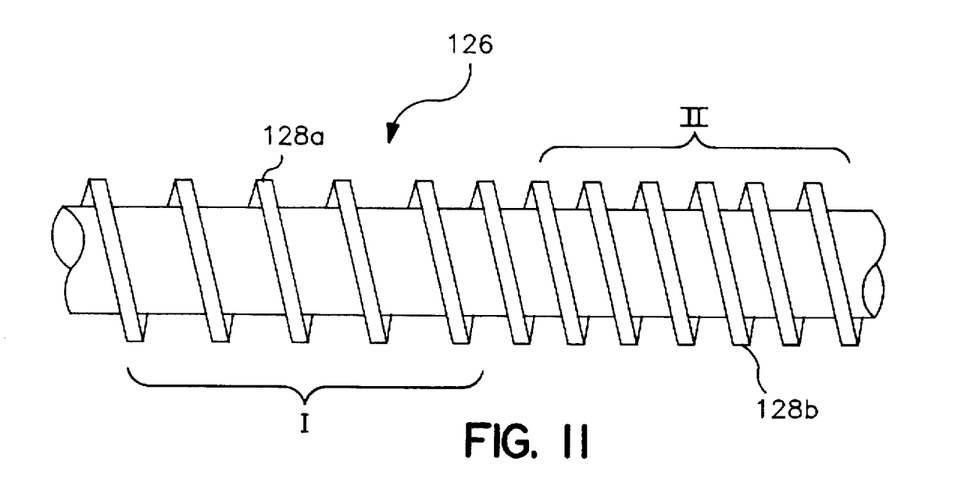
FIG. 11 is a view of an alternate screw design for use in connection with the present invention.

In another example, the pitch of the threads may vary over the length of the screw. Referring now to FIG. 11, where one embodiment of a variable pitch screw 126 is depicted. The threads 128a in Section I of the screw 126 have a larger pitch or spacing than do the threads 128b in Section II. One potential advantage for such a design is that axial compression, i.e., movement of the ends of the stent towards each other, can be increased at the beginning of the release sequence when the thread pitch is larger, followed by more precise control over the rate of radial expansion of the stent when the thread pitch is smaller. Other modifications in the use of varying thread pitch will also be possible, e.g., providing a smaller thread pitch first followed by a larger pitch, continually varying the pitch over the length of the screw portion, etc.

Furthermore, the stent could also include an expandable sheath or covering to provide support between the individual wire or wires forming the stent. Such a covering would preferably be attached to the stent such that winding of the stent about the inner sheath would also result in winding of the covering to reduce the overall profile of the device during insertion. Alternatively, other means of reducing the profile of such a covering could be provided.

Although the preferred embodiment illustrates the use of one threaded member operatively connecting the inner and outer sheaths 40 and 50 such that rotation of the inner and outer sheaths relative to each other results in corresponding controlled relative axial movement of the inner and outer sheaths 40 and 50, those skilled in the art will understand that variations involving the location of the threaded portion fall within the scope of the present invention. Examples of some variations include locating the threaded portion on the second handle, threading the inner and outer sheaths themselves, etc. Those skilled in the art will also understand that other devices incorporating a variety of elements, such as motors, gears, a rack and pinion, combinations of the above, etc., could be used to provide simultaneous rotation of the ends of the stent 70 about the longitudinal axis with a corresponding controlled axial movement of the ends of the stent.

The preceding specific embodiments are illustrative of the practice of the invention. It is to be understood, however, that other expedients known to those skilled in the art or disclosed herein, may be employed without departing from the scope of the appended claims.

What is claimed is:

1. A system for delivering a radially expandable stent for implantation within a body vessel, comprising:

an elongated tubular member comprising an inner sheath having a proximal end and a distal end and an outer sheath having a proximal end and a distal end, the outer sheath having a lumen for at least partially receiving the inner sheath, the distal end of the inner sheath extending past the distal end of the outer sheath;

a self-expanding intraluminal stent located over the distal end of the inner sheath, the stent having a proximal end attached to the distal end of the outer sheath and a distal end attached to the distal end of the inner sheath;

means for controllably rotating the inner sheath relative to the outer sheath and simultaneously controllably moving the inner sheath axially relative to the outer sheath.

2. A system according to claim 1, wherein the means for controllably rotating the inner sheath relative to the outer sheath comprises operatively mounting the inner and outer sheaths on a threaded member, whereby rotation of one of the sheaths causes controlled axial displacement of the inner and outer sheaths relative to each other.

3. A system according to claim 1, wherein the means for controllably rotating the inner sheath relative to the outer sheath comprises a first handle attached to the inner sheath;

a second handle attached to the outer sheath, wherein the first and second handles are operatively mounted on a screw such that rotation of one handle relative to the other handle results in controlled axial movement of the inner and outer sheaths relative to each other.

4. A system according to claim 1, further comprising a first release wire extending from the proximal end of the elongated tubular member to the distal end of the inner sheath of the elongated tubular member, wherein the first release wire retains the distal end of the stent against the distal end of the inner sheath, and a second release wire extending from the proximal end of the elongated tubular member to the distal end of the outer sheath of the elongated tubular member, wherein the second release wire retains the proximal end of the stent against the distal end of the outer sheath.

5. A system according to claim 4, further comprising a first release wire actuator operatively connected to the first release wire and a second release wire actuator operatively connected to the second release wire.

6. A system according to claim 5, wherein the proximal and distal ends of the stent further comprise openings formed therein.

7. A system according to claim 6, further comprising a first suture threaded through the opening in the distal end of the stent, the first suture operatively connected to the first release wire, whereby axial movement of the first release wire releases the first suture and the distal end of the stent, the system further comprising a second suture threaded through the opening in the proximal end of the stent, the second suture operatively connected to the second release wire, whereby axial movement of the second release wire releases the second suture and the proximal end of the stent.

8. A system for delivering a radially expandable stent for implantation within a body vessel, comprising:

an elongated tubular member comprising an inner sheath having a proximal end and a distal end and an outer sheath having a proximal end and a distal end, the outer sheath having a lumen for at least partially receiving the inner sheath, the distal end of the inner sheath extending past the distal end of the outer sheath;

a self-expanding intraluminal stent located over the distal end of the inner sheath, the stent having a proximal end attached to the distal end of the outer sheath and a distal end attached to the distal end of the inner sheath;

a first handle operatively attached to the inner sheath, the first handle located at the proximal end of the inner sheath;

a second handle operatively attached to the outer sheath, the second handle located at the proximal end of the outer sheath; and the first and second handles being operatively mounted on a screw such that rotation of one handle relative to the other handle results in controlled axial movement of the inner and outer sheaths relative to each other.

9. A system according to claim 8, further comprising a release wire extending from the proximal end of the elongated tubular member to the distal end of the elongated tubular member, wherein the release wire retains the proximal end of the stent against the distal end of the outer sheath and the distal end against the distal end of the inner sheath.

10. A system according to claim 9, further comprising a release wire actuator operatively connected to the release wire.

11. A system according to claim 8, further comprising a first release wire extending from the proximal end of the elongated tubular member to the distal end of the inner sheath of the elongated tubular member, wherein the first release wire retains the distal end of the stent against the distal end of the inner sheath, and a second release wire extending from the proximal end of the elongated tubular member to the distal end of the outer sheath of the elongated tubular member, wherein the second release wire retains the proximal end of the stent against the distal end of the outer sheath.

12. A system according to claim 11, further comprising a first release wire actuator operatively connected to the first release wire and mounted on the first handle and a second release wire actuator operatively connected to the second release wire and mounted on the second handle.

13. A system according to claim 11, wherein the proximal and distal ends of the stent further comprise openings formed therein.

14. A system according to claim 13, further comprising a first suture threaded through the opening in the distal end of the stent, the first suture operatively connected to the first release wire, whereby axial movement of the first release wire releases the first suture and the distal end of the stent, the system further comprising a second suture threaded through the opening in the proximal end of the stent, the second suture operatively connected to the second release wire, whereby axial movement of the second release wire releases the second suture and the proximal end of the stent.

15. A method for controllably delivering a self-expandable stent comprising steps of:

providing a stent delivery device comprising:
an elongated tubular member comprising an inner sheath having a proximal end and a distal end and an outer sheath having a proximal end and a distal end, the outer sheath having a lumen for at least partially receiving the inner sheath, the distal end of the inner sheath extending past the distal end of the outer sheath;
a self-expanding intraluminal stent located over the distal end of the inner sheath, the stent having a proximal end retained against the distal end of the outer sheath and a distal end retained against the distal end of the inner sheath; means for controllably rotating the inner sheath relative to the outer sheath and simultaneously controllably moving the inner sheath axially relative to the outer sheath;
inserting the stent delivery device to locate the stent in a desired position within a body lumen;
rotating the inner sheath and outer sheath relative to each other, whereby the stent is expanded radially;
releasing one of the proximal and distal ends of the stent; and
releasing the other of the proximal and distal ends of the stent.

16. A method according to claim 15, wherein the controlled axial movement comprises movement of the distal end of the inner sheath towards the distal end of the outer sheath.

17. A method according to claim 15, wherein the steps of releasing the proximal and distal ends of the stent are performed at the same time.

18. A method according to claim 15, wherein the means for controllably rotating the inner sheath relative to the outer sheath comprises operatively mounting the inner and outer sheaths on a threaded member, whereby rotation of one of the sheaths causes controlled axial displacement of the inner and outer sheaths relative to each other.

19. A method according to claim 15, wherein the means for controllably rotating the inner sheath relative to the outer sheath comprises a first handle attached to the inner sheath;
a second handle attached to the outer sheath, wherein the first and second handles are operatively mounted on a screw such that rotation of one handle relative to the other handle results in controlled axial movement of the inner and outer sheaths relative to each other.

20. A method according to claim 19, wherein the stent delivery device further comprises a first release wire extending from the proximal end of the elongated tubular member to the distal end of the inner sheath of the elongated tubular member, the first release wire retaining the distal end of the stent against the distal end of the inner sheath, and a second release wire extending from the proximal end of the elongated tubular member to the distal end of the outer sheath of the elongated tubular member, the second release wire retaining the proximal end of the stent against the distal end of the outer sheath, and further wherein the steps of releasing the ends of the stent comprise moving the first and second release wires axially.

21. A method according to claim 21, wherein the stent delivery device further comprises a first release wire actuator operatively connected to the first release wire and mounted on the first handle and a second release wire actuator operatively connected to the second release wire and mounted on the second handle, wherein the steps of moving the first and second release wires axially are performed by operating the first and second release wire actuators.

22. A method for controllably delivering a self-expandable stent comprising steps of:

providing a stent delivery device comprising:
an elongated tubular member comprising an inner sheath having a proximal end and a distal end and an outer sheath having a proximal end and a distal end, the outer sheath having a lumen for at least partially receiving the inner sheath, the distal end of the inner sheath extending past the distal end of the outer sheath;
a self-expanding intraluminal stent located over the distal end of the inner sheath, the stent having a proximal end retained against the distal end of the outer sheath and a distal end retained against the distal end of the inner sheath; a first handle operatively attached to the inner sheath, the first handle located at the proximal end of the inner sheath;
a second handle operatively attached to the outer sheath, the second handle located at the proximal end of the outer sheath; and
the first and second handles being operatively mounted on a screw such that rotation of one handle relative to the other handle results in controlled axial movement of the inner and outer sheaths relative to each other;
inserting the stent delivery device to locate the stent in a desired position within a body lumen;
rotating the first and second handles relative to each other using the screw, whereby the stent is expanded radially
releasing one of the proximal and distal ends of the stent; and
releasing the other of the proximal and distal ends of the stent.

* * * * *